(12) United States Patent
Han et al.

(10) Patent No.: US 12,268,537 B2
(45) Date of Patent: Apr. 8, 2025

(54) VISIBLE LIGHT PROJECTION INDICATOR FOR DENTAL X-RAY IMAGING APPARATUS AND METHOD OF USING SAME

(71) Applicant: Fangkai HAN, Shanghai (CN)

(72) Inventors: Fangkai Han, Shanghai (CN); Jue Li, Shanghai (CN)

(73) Assignee: Fangkai Han, Shanghai (CN)

( * ) Notice: Subject to any disclaimer, the term of this patent is extended or adjusted under 35 U.S.C. 154(b) by 211 days.

(21) Appl. No.: 18/106,772

(22) Filed: Feb. 7, 2023

(65) Prior Publication Data

US 2023/0263486 A1  Aug. 24, 2023

Related U.S. Application Data

(63) Continuation-in-part of application No. PCT/CN2020/126050, filed on Nov. 3, 2020.

(30) Foreign Application Priority Data

Aug. 7, 2020 (CN) .......................... 202010789470.6
Aug. 10, 2020 (CN) .......................... 202010795582.2

(Continued)

(51) Int. Cl.
    *A61B 6/08* (2006.01)
    *A61B 6/51* (2024.01)

(52) U.S. Cl.
    CPC . *A61B 6/08* (2013.01); *A61B 6/51* (2024.01)

(58) Field of Classification Search
    CPC .................................... A61B 6/08; A61B 6/51
    See application file for complete search history.

(56) References Cited

U.S. PATENT DOCUMENTS 9,439,619 B1    9/2016 Nance et al.
2006/0126796 A1  6/2006 Hecker

FOREIGN PATENT DOCUMENTS

CN    201847692 U    6/2011
CN    202891970 U    4/2013
(Continued)

OTHER PUBLICATIONS

Basic Operation of Oral and Maxillofacial Conventional X-ray Practices, WS-ICS; 2018, 21 pgs.
(Continued)

*Primary Examiner* — Dani Fox
*Assistant Examiner* — Fani Polyzos Boosalis
(74) *Attorney, Agent, or Firm* — BLANK ROME LLP

(57) ABSTRACT

A visible light projection indicator for a dental x-ray imaging apparatus, including a casing (2), one end of the casing (2) detachably affixed to a beam-limiting cone (3) in the dental x-ray imaging apparatus, the other end thereof provided with a light exit aperture; a visible light source (1) positioned in the casing (2) and configured to be able to emit visible light; the casing (2) affixed to the beam-limiting cone (3) so as to form a light passage so that visible light emitted from the visible light source (1) is able to travel along the light passage and exits from the light exit aperture. A method of using a visible light projection indicator for a dental x-ray imaging apparatus, including the steps of: affixing the visible light projection indicator to a beam-limiting cone (3); activating at least one visible light source (1) to cause visible light to be emitted from a light exit aperture of the visible light projection indicator; according to a light field (6) of the visible light, adjusting a distance and an orientation of the beam-limiting cone (3) from and with respect to an object to be imaged so that the visible light is aligned with a center of (Continued)

an area (5) to be imaged; and performing an X-ray imaging operation.

15 Claims, 10 Drawing Sheets

(30) Foreign Application Priority Data

Aug. 10, 2020 (CN) .......................... 202010797643.9
Aug. 25, 2020 (CN) .......................... 202010861840.2

(56) References Cited

FOREIGN PATENT DOCUMENTS

| CN | 103126691 A | 6/2013 | | |
|---|---|---|---|---|
| CN | 103369789 A | 10/2013 | | |
| CN | 204445917 U | 7/2015 | | |
| CN | 205994516 U | 3/2017 | | |
| CN | 106974673 A | 7/2017 | | |
| CN | 208268826 U | 12/2018 | | |
| CN | 109172001 A | 1/2019 | | |
| CN | 209032420 U | 6/2019 | | |
| CN | 110859641 A | 3/2020 | | |
| CN | 211022722 U | 7/2020 | | |
| CN | 213551885 U | 6/2021 | | |
| CN | 213606457 U | 7/2021 | | |
| CN | 213640925 U | 7/2021 | | |
| JP | H-0852162 A | 2/1996 | | |
| JP | H-09313482 A | 12/1997 | | |
| KR | 10-20140037314 A | 3/2014 | | |
| WO | WO-2006034984 A1 | * | 4/2006 | ............. A61B 6/035 |
| WO | WO-2017/047933 A1 | | 3/2017 | |
| WO | WO-2021205076 A1 | * | 10/2021 | ............. A61B 6/032 |

OTHER PUBLICATIONS

International Search Report for PCT/CN2020/126050, dated Apr. 28, 2021, 2 pgs.
Decision of Rejection, CN202010795582.2, 9 pages; English Translation, 9 pages.
Decision of Rejection, CN202010789470.6, 7 pages; English Translation, 6 pages.
Decision of Rejection, CN202010797643.9, 8 pages; English Translation, 8 pages.

* cited by examiner

VISIBLE LIGHT PROJECTION INDICATOR FOR DENTAL X-RAY IMAGING APPARATUS AND METHOD OF USING SAME

RELATED APPLICATIONS

This application is a continuation-in-part of PCT/CN2020/126050, filed on Nov. 3, 2020, which claims priority to Chinese Application No. 202010795582.2, filed on Aug. 10, 2020, Chinese Patent Application No. 202010789470.6, filed on Aug. 7, 2020, Chinese Patent Application No. 202010797643.9, filed on Aug. 10, 2020 and Chinese Patent Application No. 202010861840.2, filed on Aug. 25, 2020. The entire contents of these applications are hereby incorporated by reference.

FIELD OF THE INVENTION

The present disclosure relates to the field of oral and maxillofacial imaging technology and, in particular, to a visible light projection indicator for a dental x-ray imaging apparatus and a method of using it.

DESCRIPTION OF THE PRIOR ART

Dental x-ray imaging apparatuses are often used in oral diagnosis and treatment. Such an apparatus is typically composed of a tube that generates X-rays and a cylindrical beam-limiting conenested therewith. X-rays from the tube are irradiated from the beam-limiting cone on a patient's face in the shape of a cone or cylinder. The closer the tube is, the smaller a radiation field will be obtained. The farther the tube is, the bigger a radiation field will be obtained. In clinical use, a physician places a film on the inner surface of teeth within a patient's mouth, and then adjusts an orientation of the beam-limiting cone so that an exit of the beam-limiting cone is aligned with the tooth surface to be imaged, with a centerline of the beam-limiting cone crossing the film at right angles at a center thereof. This can prevent distortion of an image taken of the teeth and ensure a radiation field that encompasses the entire tooth surface to be imaged.

However, although this X-ray projection technology for dental imaging is theoretically plausible, its practical implementation is unsatisfactory since it relies only on the alignment of the beam-limiting cone. As X-rays are invisible light, they are neither measurable nor predictable in practical use. For this reason, the beam-limiting cone alignment approach lacks practical implementability and is absent of a definitive light field for indication. Therefore, it is prone to significant errors in clinical practice and practical implementation, not standardized in terms of clinical practice and lack of theoretical rigorousness.

In addition, as the film that receives X-rays must be placed in the patient's mouth, real-time display of an X-ray image would be difficult to achieve by a digital technique. Further, even if such real-time display is possible, the subsequent imaging at a determined position may lead to excessive exposure to X-rays. Therefore, at present, disposable chemical films are still being used for this purpose.

In practice, if the patient closes his/her teeth or lips after the film is placed in the mount, the physician has to rely on his/her experience to subjectively determine whether the centerline is perpendicular to the tooth surface or film and aligned with the center of the film and whether the X-ray field accurately encompasses the tooth surface to be imaged. Moreover, whether an appropriate image has been captured can be confirmed only after the film has been developed. Moreover, if there is a deviation, it may be necessary to recapture another image. This prolongs the time spent for imaging and increases the patient's exposure to X-rays.

Specifically, two techniques are mainly in oral and maxillofacial X-ray periapical radiography: bisecting-angle and paralleling. However, as detailed below, limited by the current standards and techniques, as well as by the conventional designs of dental imaging apparatuses, a physician is not able to accurately identify an X-ray field during a dental radiographic process.

I. Bisecting-Angle Technique

Basic Operation of Oral and Maxillofacial Conventional X-Ray Practices, a standard (WS/T 608-2018) issued by the National Health Commission of the People's Republic of China (PRC) for the health industry in the country (released on May 10, 2018 and implemented on Nov. 1, 2018), requires, in X-ray periapical radiography, a central X-ray to be perpendicular to a line bisecting an angle between an long axis of a tooth being treated and an image receptor medium.

Regarding projection in this technique, the guideline makes the following recommendations on its position on the body surface:

a) When projecting onto a maxillary tooth, given an imaginary line passing through the upper edge of the external auditory meatus and the tip of the nose, the central X-ray passes 1) the tip of the nose in case of projecting onto a maxillary central incisor; 2) a midpoint of a line segment connecting the tip of the nose and the ala of the nose on the same side in case of projecting onto a maxillary central or lateral incisor on the side; or the ala of the nose on the same side in case of projecting onto a maxillary cuspid.

b) When projecting onto any mandibular tooth, the central X-ray travels along an imaginary line 10 mm above the lower edge of the mandible so as to be aligned with the location of the tooth being treated.

As can be seen from this specification about bisecting-angle projection for the maxillary and mandibular front teeth, this technique locates the spatial position of a tooth by estimation and prediction based on alignment with external soft tissue landmarks. In practical clinical applications, a beam-limiting cone of an X-ray tube is roughly aligned with a body landmark, and it is impossible to precisely determine a projection location, a projection direction and a projection angle before an image is taken. Undoubtedly, this technique will introduce significant errors and uncertainties to clinical images.

The arbitrariness and uncertainty in the determination of a projection location based on a body landmark are not a real reflection of the essence and attributes of the bisecting-angle technique.

II. Periapical Paralleling Technique

The periapical paralleling technique, also known as the right-angle technique, long-beam-limiting cone technique, or long focal length paralleling technique, operates by placing an X-ray film in parallel to a long axis of a tooth and projecting a central X-ray perpendicular both to the long axis of the tooth and to the film. Theoretically, taking an image in this way is advantageous in that there is little distortion between the image and the real tooth. In order to ensure parallelism of the film to the long axis of the tooth, the film has to be placed slightly away from the film. Moreover, a high voltage and a fast film are used to reduce the time and amount of exposure. However, this method is often used in experimental settings and not suitable for clinical applications. It requires the use of necessary supporting tools, considerable time consumption and occupation of a relatively large intra-oral space for the placement of the film. As seen in clinical practice, in most cases, the parallelism of a film to a long axis of a tooth cannot be ensured within the oral cavity due to an inclination of the teeth, the morphology, thickness and other factors of the surrounding soft tissues (the tongue, the floor of the mouth and the palate) and bones (the alveolar bone, the palatal arch), the volume of the oral cavity and difficulties of patient cooperation. Despite the theoretical feasibility, its value in clinical practice is limited.

Therefore, still further improvement and progress would be desirable in the prior art.

SUMMARY OF THE INVENTION

In view of the above-described drawbacks of the prior art, it is an object of the present invention to provide a visible light projection indicator for a dental x-ray imaging apparatus, which is capable of rapidly and definitely locating an aligned target site to be imaged during imaging of a patient's tooth using the dental imaging apparatus.

The above object is attained by a visible light projection indicator for a dental x-ray imaging apparatus provided in the present invention, which comprises a casing, one end of the casing detachably affixed to a beam-limiting cone in the dental x-ray imaging apparatus, the other end thereof provided with a light exit aperture; a visible light source positioned in the casing and configured to be able to emit visible light; a light passage being formed after the casing is affixed to the beam-limiting cone so that visible light emitted from the visible light source is able to travel along the light passage and exits from the light exit aperture.

Further, a centerline of the casing is coincident with a centerline of the beam-limiting cone.

Further, an inner diameter of the casing is equal to an inner diameter of the beam-limiting cone.

Further, a light source switch is also included, which is provided on an outer side of the casing.

Further, an infrared sensor is also included, which is provided at an edge of the light exit aperture and used to sense the position of an object to be imaged.

Further, the light exit aperture is covered with a transparent cover.

Further, the transparent cover is provided at its center with a light-shading mark for indicating an area where the visible light is projected.

Further, a magnetic structure is provided on an end face of the casing opposing the light exit aperture, and the casing is configured to be able to be attractively affixed to the beam-limiting cone through the magnetic structure.

Further, the visible light source is arranged on an inner wall of the casing, and the casing is provided therein with a light-reflecting plate, which is placed obliquely with respect to the inner wall of the casing so that a position of a virtual image of the visible light source formed by the light-reflecting plate coincides with a position of an X-ray source in the dental x-ray imaging apparatus in a direction perpendicular to an opening of the beam-limiting cone.

Further, a mirror surface of the light-reflecting plate faces the light exit aperture and is inclined at an angle of 45° with respect to the inner wall of the casing, and the visible light source is arranged on the inner wall of the casing between the mirror surface and the light exit aperture so that the virtual image of the visible light source formed by the light-reflecting plate is located with the extent of the opening of the beam-limiting cone.

Further, a convex lens is also included, which is disposed between the light-reflecting plate and the light exit aperture.

Further, the visible light source includes an LED light.

Further, the casing includes an annular base, and the visible light source is mounted in the annular base.

Further, the casing further comprises a double-layer cylindrical structure connected to openings at opposing ends of the annular base, the double-layer cylindrical structure comprising an inner tube disposed on an inner side and an outer tube disposed on an outer side, the light passage being formed between an outer surface of the inner tube and an inner surface of the outer tube.

Further, the outer surface of the inner tube and the inner surface of the outer tube are made of a reflective material.

Further, the inner tube has a smaller radius at one end proximal to the annular base than at one end away from the annular base.

Further, two laser light sources are also included, which are respectively arranged on the annular base and is radially symmetrical with respect to a center of the annular base and emitting light beams intersecting ahead of the light exit aperture.

Further, the annular base is an integral structure.

Further, the annular base is provided on an inner surface thereof with a first elastic member.

Further, the annular base comprises a plurality of base elements, each the base element being connected to each other by second elastic members.

The present invention also discloses a method of using a visible light projection indicator for a dental x-ray imaging apparatus, comprising steps of:
a) affixing the visible light projection indicator to a beam-limiting cone in the dental x-ray imaging apparatus;
b) activating a visible light source in the visible light projection indicator to cause visible light to be emitted from a light exit aperture of the visible light projection indicator;
c) according to a light field of the visible light, adjusting a distance and an orientation of the beam-limiting cone from and with respect to an object to be imaged so that the visible light is aligned with a center of an area to be imaged; and
d) performing an X-ray imaging operation.

The present invention also discloses a dental x-ray imaging apparatus, comprising: an X-ray source; a body for housing the X-ray source; a beam-limiting cone disposed externally around the X-ray source and extending out of the body; a visible light projection indicator comprising: a casing, one end of the casing affixed to the beam-limiting cone, the other end thereof provided with a light exit aperture; a visible light source positioned in the casing and configured to be able to emit visible light; a light passage being formed after the casing is affixed to the beam-limiting cone so that visible light emitted from the visible light source is able to travel along the light passage and exits from the light exit aperture.

Further, a centerline of the casing is coincident with a centerline of the beam-limiting cone.

Further, the visible light source is arranged on an inner wall of the casing, and the casing is provided therein with a light-reflecting plate, which is placed obliquely with respect to the inner wall of the casing so that a position of a virtual image of the visible light source formed by the light-reflecting plate coincides with a position of the X-ray source in a direction perpendicular to an opening of the beam-limiting cone.

Further, a convex lens is also included, which is disposed between the light-reflecting plate and the light exit aperture.

Further, the casing includes an annular base, and the visible light source is mounted in the annular base.

Further, the casing also comprises a double-layer cylindrical structure connected to openings at opposing ends of the annular base, the double-layer cylindrical structure comprising an inner tube disposed on an inner side and an outer tube disposed on an outer side, the light passage being formed between an outer surface of the inner tube and an inner surface of the outer tube.

Further, the outer surface of the inner tube and the inner surface of the outer tube are made of a reflective material.

Further, the inner tube has a smaller radius at one end proximal to the annular base than at one end away from the annular base.

Further, two laser light sources are also included, which are respectively arranged on the annular base and is radially symmetrical with respect to a center of the annular base and emitting light beams intersecting ahead of the light exit aperture.

Below, the concept, structural details and resulting technical effects of the present application will be further described with reference to the accompanying drawings to provide a full understanding of the objects, features and effects of the invention.

DETAILED DESCRIPTION OF THE PREFERRED EMBODIMENTS

Figure 1:
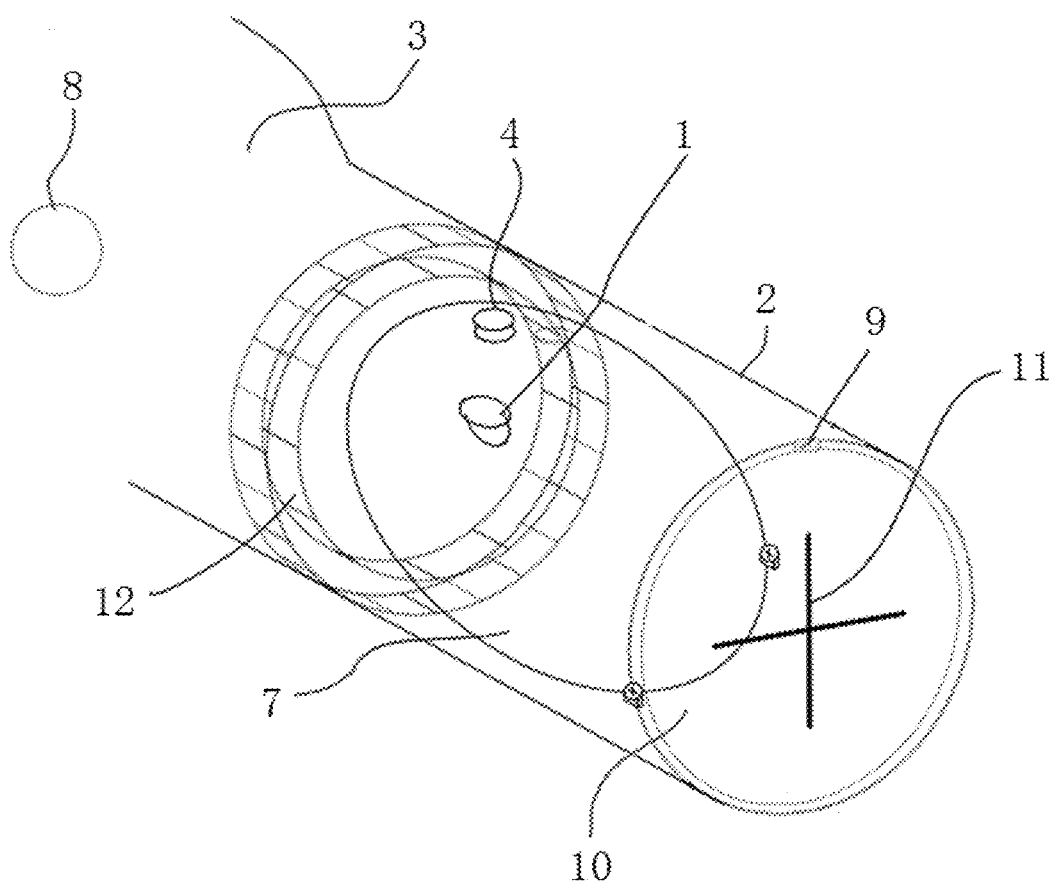
FIG. 1 is a schematic perspective assembly view of a first embodiment of the present disclosure.

Below, the accompanying drawings of this specification are referenced to introduce many preferred embodiments of the present application so that the techniques thereof become more apparent and readily understood. This application may be embodied in many different forms of embodiment, and the protection scope of the application is not limited only to the embodiments mentioned herein.

Throughout the accompanying drawings, structurally identical parts are indicated with identical reference numerals, and structurally or functionally similar components are indicated with similar reference numerals. The size and thickness of each component in the drawings are arbitrarily depicted, and the present application is not limited to any size or thickness of each component. For greater clarity of illustration, the thicknesses of some parts are exaggerated as appropriate somewhere in the drawings.

A dental x-ray imaging apparatus takes an image using X-rays irradiated on a patient's face, which then travel though tissues such as gingivae and the alveolar bone and reach a specially made dental film that has been placed in the oral cavity. Such apparatuses feature low output power and a beam-limiting cone with a very small radiation field and high directivity allowing direct alignment with a target site to be examined. A dental x-ray imaging apparatus is usually equipped with a combined set of projection heads. After a patient has been positioned as desired, X-rays can be projected onto any intended tooth in a proper direction simply by moving the projection heads. A dental X-ray imaging apparatus may also employ a hand-held design integrating a projection head with a beam-limiting cone, which is also capable of projecting X-rays onto any intended tooth in a proper direction.

The beam-limiting cone is a metal barrel in the shape of a circular cylinder or cone. Sometimes, it is lined with thin lead for enhanced shielding and protection against X-rays. During projection, it relies mainly on the blockage and absorption of X-rays by a wall of the barrel to limit a radiation field. Therefore, the size of the radiation field may be determined by a length and a diameter of the beam-limiting cone. Generally, the radiation field is circular.

Embodiment 1

Figure 2:
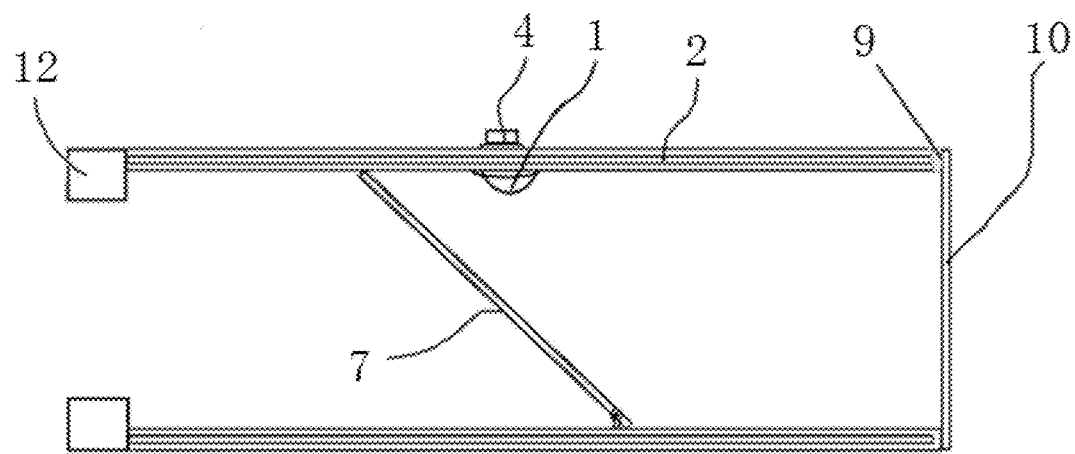
FIG. 2 is a schematic axial cross-sectional view of the first embodiment of the present disclosure.

FIGS. 1 and 2 show a visible light projection indicator for a dental x-ray imaging apparatus, which includes at least one visible light source 1 arranged on a cylindrical inner wall surface of a cylindrical light projection casing 2. During use, the light projection casing 2 is fixedly attached to a beam-limiting cone 3, and once a light source switch 4 is activated, visible light is emitted from the visible light source 1, directly or indirectly propagates along the cylindrical inner wall surface, exits from a light exit aperture and strikes an area 5 to be imaged, such as a patient's face, lip or cheek area outside and aligned with a tooth. Only one visible light source 1 may be provided, and part of light emitted therefrom may propagate along the inner wall surface and strike the area 5 to be imaged. Alternatively, a plurality of visible light sources 1 may be arranged circumferentially around the inner wall surface, and light emitted therefrom may propagate along the inner wall surface and strike the area 5 to be imaged as a round circular light spot, which can more exactly indicate an area aligned with the beam-limiting cone 3.

In order to ensure that an area where the visible light is projected (light field) 6 is coincident with an X-ray field, it is necessary to ensure that the visible light exits the light exit aperture of the beam-limiting cone 3 as parallel light in conformity with an opening of the beam-limiting cone 3 and strikes the area 5 to be imaged.

Specifically, the light projection casing 2 may be detachably secured at the opening of the beam-limiting cone 3 in such a manner that a centerline of the light projection casing 2 coincides with a centerline of the beam-limiting cone 3. An inner diameter of the light projection casing 2 is equal to an inner diameter of the beam-limiting cone 3. In other words, the light projection casing 2 may be considered as an extension of the beam-limiting cone 3.

Figure 3:
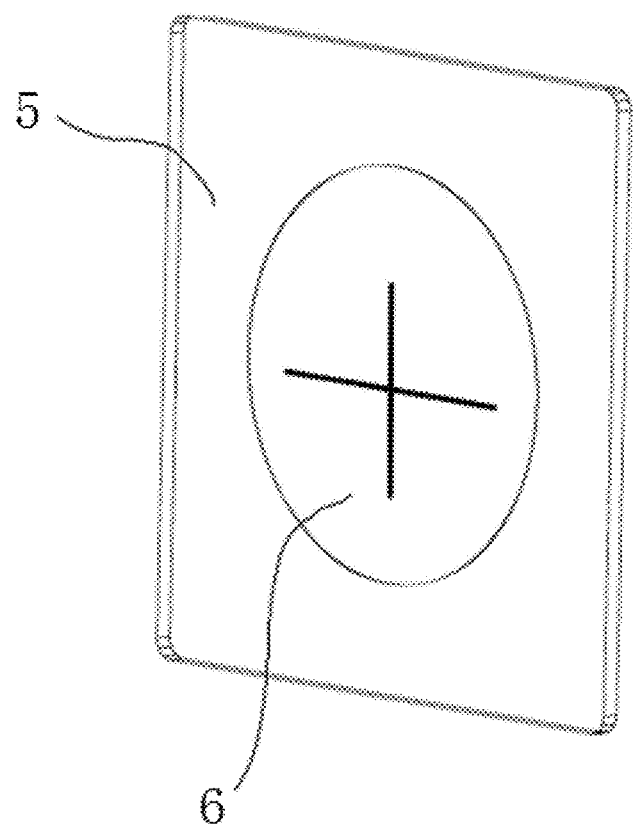
FIG. 3 schematically illustrates a light field in the first embodiment of the present disclosure.

In some examples, an oblique light-reflecting plate 7 is disposed in the interior of the light projection casing 2 delimited by the cylindrical inner wall surface, and the visible light source 1 is arranged above a light-reflecting surface of the light-reflecting plate 7. Moreover, part of the visible light emitted from the visible light source 1 that travels deeper into the beam-limiting cone 3 strikes, and is reflected by, the light-reflecting plate 7 so as to also exit from the light exit aperture. That is, under the action of the light-reflecting plate 3, all the visible light emanated from the visible light source 1 travels along the inner wall surface and exits from the light exit aperture. As a result, a circular light spot having the same shape as a cross-sectional shape of the inner wall surface is formed. In addition, since the inner diameter of the light projection casing 2 is equal to that of the beam-limiting cone 3, keeping the circular light spot in the same shape as the opening of the beam-limiting cone 3 is equivalent to extending the beam-limiting cone 3 to the area 5 to be imaged. As shown in FIG. 3, as the light field 6 formed on the area 5 to be imaged is visible to an operator, it can considerably facilitate adjustment and focusing operations performed by the operator.

Considering that the light field 6 should coincide with the X-ray field, an image position of the visible light source 1 on the light-reflecting plate 7 is coincident with the position of an X-ray source 8 in the dental imaging apparatus radially with respect to the cylindrical inner wall surface. Of course, it is more preferred that the image position of the visible light source 1 totally coincides with the position of the X-ray source 8 because in this way, it can be ensured that the light field 6 remains in complete coincidence with the X-ray field regardless of its distance from the area 5 to be imaged.

Specifically, a mirror surface of the light-reflecting plate 7 may be oriented to form an angle of 45° with the cylindrical inner wall surface and to face the light exit aperture. Additionally, the visible light source 1 is disposed on the inner wall surface between the mirror surface and the light exit aperture, and a virtual image of the visible light source 1 formed in the light-reflecting plate 7 is positioned within the extent of the opening of the beam-limiting cone 3.

Further, the light-reflecting plate 7 is completely transparent to X-rays. That is, the presence of the light-reflecting plate 7 does not affect the passage of X-rays emitted from the X-ray source 8 that is disposed in a tube through the beam-limiting cone 3 or their irradiation on the area 5 to be imaged at all.

In some examples, an infrared sensing area is provided at a location at an edge of the light exit aperture, which does not block the visible light, or blocks it only to a minor extent, and an associated infrared sensor 9 is provided at the edge of the light exit aperture. The infrared sensor 9 includes an infrared transmitter for transmitting infrared radiation and an infrared receiver for receiving infrared radiation. By doing this, a position of a human body can be sensed to serve as a basis for controlling light emission of the visible light source 1. Specifically, when a given part of the human body, such as a hand or face, is present in a region that is irradiated with the infrared radiation from the infrared transmitter and thus allows infrared sensing, for example, 20 cm ahead, it will reflect part of the infrared radiation. After being received by the infrared receiver, this part of the infrared radiation may undergo necessary processing, and a signal may be produced, which controls the visible light source 1 to emit light, for example, for 30 seconds. Correspondingly, when the human body leaves the infrared sensing range, the visible light source 1 may stop emitting light. The infrared sensor 9 may be implemented as is conventional and, therefore, needs not be described in further detail herein.

In some examples, the light exit aperture is covered with a transparent cover 10, which has anti-glare properties and can additionally ensure accurate focusing during imaging.

In some examples, a light-shading mark 11, for example, in the shape of the symbol "+", as shown in FIG. 3, may be provided at a center of the transparent cover 10. By doing so, when the visible light is irradiated on the area 5 to be imaged, a shadow of the light-shading mark 11 will be present at a center of the light field 6 to indicate the position of the center of the light field 6. This can additionally facilitate position and angle adjustment of the beam-limiting cone 3 by an operator for exact alignment with a center of the film.

The light projection casing 2 is attached before X-ray imaging in order to facilitate angle and position adjustment of the beam-limiting cone 3, but should be detached thereafter because it may affect the X-ray field if it is still present during the imaging process. In order to facilitate the attachment and detachment, at a bottom end of the light projection casing 2 opposing the light exit aperture, a magnetic structure 12 may be provided, which can help in assembly and securing. This is because the beam-limiting cone 3 is usually made of a ferrous material and therefore can be magnetically attracted to secure the light projection casing 2. Moreover, its detachment is easy. If the beam-limiting cone 3 is made of a non-ferrous material, another magnetic structure with the same or opposite polarity may be secured in advance at the opening of the beam-limiting cone 3.

Considering that the visible light source 1 is desired not to be bulky and to provide high illuminance, it is preferred to be an LED lamp, which is a cold light source not generating much heat.

A method of using the visible light projection indicator for a dental x-ray imaging apparatus according to this embodiment includes the steps of:
 a) fixedly attaching the light projection casing 2 to the beam-limiting cone 3;
 b) activating the light source switch 4 of the light projection casing 2 to cause visible light to be emanated from the light exit aperture of the light projection casing 2;
 c) adjusting, according to a light field 6 of the visible light, a distance and an orientation of the beam-limiting cone 3 from and with respect to an object to be imaged so as to align it with a center of an area 5 to be imaged; and
 d) performing an X-ray imaging operation.

Additionally, in some examples, the light projection casing 2 is detachably coupled to the beam-limiting cone 3, and prior to step d, the method further includes the step of: c') detaching the light projection casing 2 to avoid it from blocking X-rays.

In the visible light projection indicator for a dental x-ray imaging apparatus according to this embodiment, through attaching the cylindrical light projection casing 2 to the beam-limiting cone 3 and providing the visible light source 1 on the cylindrical inner wall surface of the light projection casing 2, visible light can be irradiated as parallel light in conformity with the opening of the beam-limiting cone 3 onto the area 5 to be imaged. Thus, before an X-ray imaging task is performed using the dental imaging apparatus, a site to be imaged can be definitely located with visible light. Based on a light field 6 of the visible light, an operator can be helped to quickly and clearly determine an area to be irradiated with X-rays and intuitively confirm whether it is the intended area, thereby reducing the possibility of required rework and reimaging due to incorrect focusing and framing that may arise from directly performing the X-ray imaging task. This embodiment is simple and reliable in structure, requires little adaptation to conventional designs and can provide a clear indication for an X-ray field.

Embodiment 2

Figure 4:
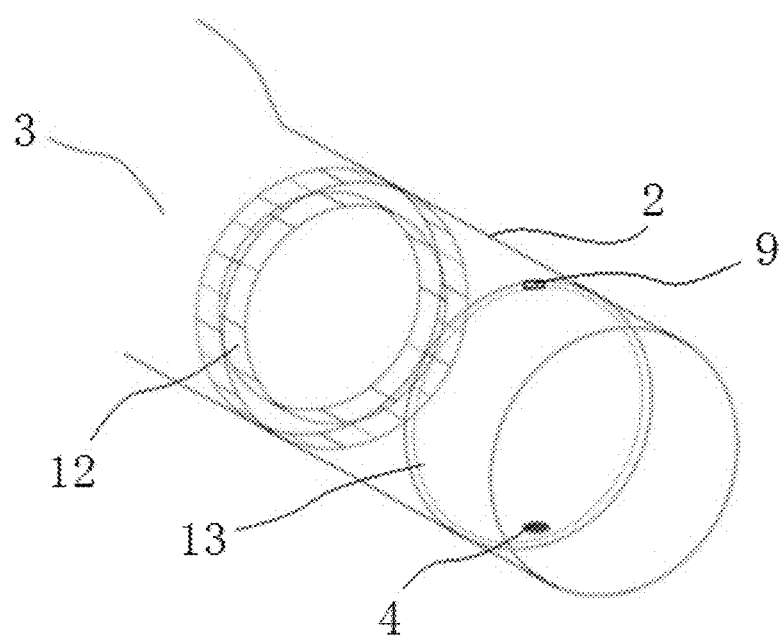
FIG. 4 is a schematic perspective assembly view of a second embodiment of the present disclosure.
Figure 5:
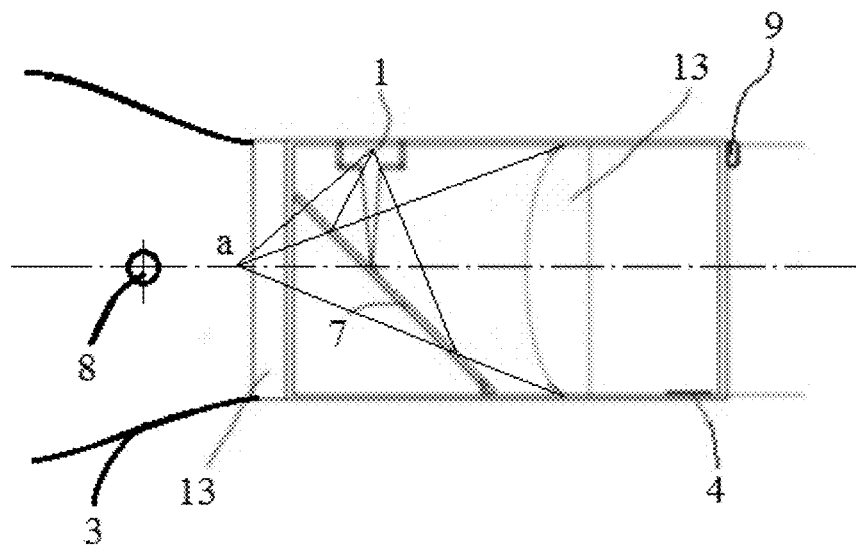
FIG. 5 schematically illustrates an axial cross-section and an optical path of the second embodiment of the present disclosure.
Figure 6:
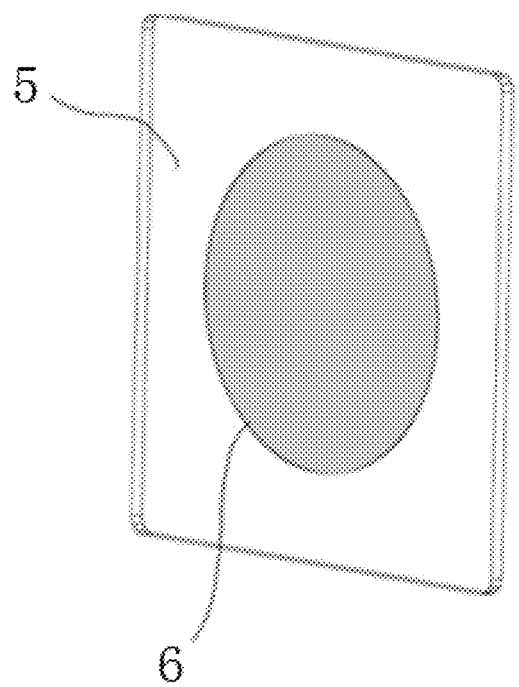
FIG. 6 schematically illustrates a light field in the second embodiment of the present disclosure.
Figure 7:
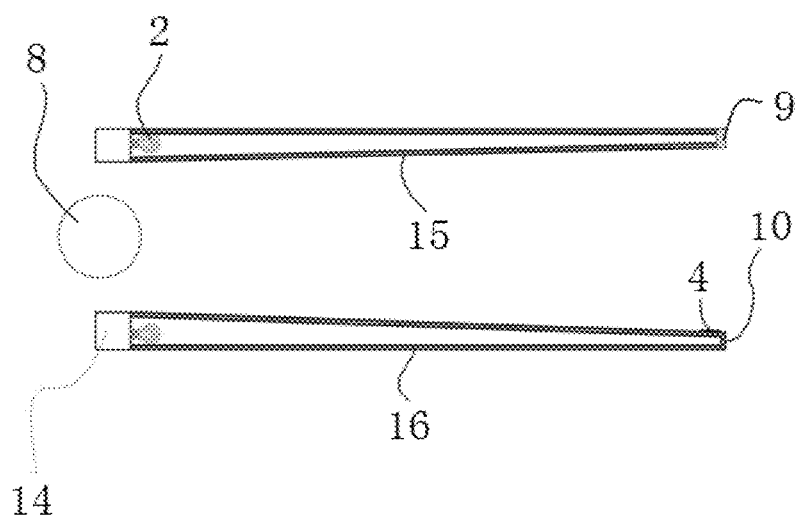
FIG. 7 is a schematic axial cross-sectional view of a third embodiment of the present disclosure.
Figure 8:
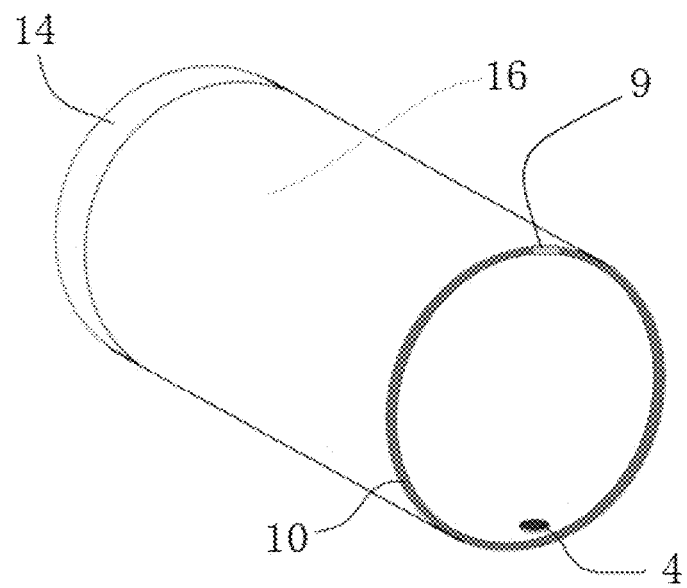
FIG. 8 is a schematic perspective view of the third embodiment of the present disclosure.

FIGS. 4, 5 and 6 show a visible light projection indicator for a dental x-ray imaging apparatus, which includes a cylindrical light projection casing 2 attached to a beam-limiting cone 3. At least one visible light source 1 is provided on a cylindrical inner wall surface of the light projection casing 2, and a light-reflecting plate 7 and a convex lens 13 are provided in the cylindrical light projection casing 2. Visible light emanated from the visible light source 1 is projected onto the light-reflecting plate 7 and reflected thereby onto the convex lens 13. It then transmits through the convex lens 13 and, as a cylindrical light beam, propagates through the beam-limiting cone 3 and exits from a light exit aperture. The light beam is a parallel beam and irradiated onto an area to be imaged.

The visible light projection indicator further includes a light source switch 4 provided on an outer wall surface of the light projection casing 2.

The visible light source 1 is an LED light that generates less heat. The visible light source 1 is arranged in the vicinity of an X-ray tube serving as an X-ray generator.

As shown in FIG. 5, the light-reflecting plate 7 is obliquely and disposed within the light projection casing 2. An image position of the visible light source 1 on the light-reflecting plate 7 is coincident with the position of an X-ray source 8 in the dental imaging apparatus radially with respect to the cylindrical inner wall surface. A mirror surface of the light-reflecting plate 7 forms an angle of 45° with an axis of the light projection casing 2 and is oriented toward the light exit aperture. The visible light source 1 is disposed on the inner wall surface between the mirror surface and the light exit aperture. The position a of a virtual image of the visible light source 1 formed by the light-reflecting plate 7 and the position a of the X-ray source 8 coincide with each other in a direction perpendicular to an opening of the beam-limiting cone 3, and both are positioned within the extent of the opening of the beam-limiting cone 3.

The light exit aperture of the light projection casing 2 is covered with a transparent cover with anti-glare properties. A magnetic structure 12 is provided at a bottom end of the light projection casing 2 by attractive affixation at the opening of the beam-limiting cone 3.

A power supply for the visible light projection indicator is rechargeable or provided by a power source for a machine.

A method of using the visible light projection indicator for a dental x-ray imaging apparatus according to this embodiment includes the steps of:

a) fixedly attaching the light projection casing 2 to the beam-limiting cone 3;

b) activating the light source switch 4 of the light projection casing 2 to cause visible light to be emanated from the light exit aperture of the light projection casing 2;

c) according to a relationship of a light field 6 and a desired area for dental imaging, horizontally or vertically adjusting obliquity of the beam-limiting cone 3 and fixing the light field 6 when a circular spot is clearly visible on a patient's face, and completing the adjustment process; and d) performing an X-ray imaging operation.

This embodiment relates to a visible light projection indicator for a dental x-ray imaging apparatus, which is used to indicate the size and extent of a radiation field. As part of a piece of X-ray examination equipment, the visible light projection indicator is mainly used for location of a target site during setup. It can mimic an X-ray field, reduce a patient dose, enhance image quality and provide a clear indication for X-ray field guidance and adjustment.

Before an X-ray imaging task is performed using the dental imaging apparatus, a site to be imaged can be definitely located with visible light. Based on a light field of the visible light, an operator can be helped to quickly and clearly determine an area to be irradiated with X-rays and intuitively confirm whether it is the intended area, thereby reducing the possibility of required rework and reimaging due to incorrect focusing and framing that may arise from directly performing the X-ray imaging task.

As shown in FIG. 6, a light field 6 visible to an operator is formed on an area 5 to be imaged (of a projection target plate), which can greatly facilitate adjustment and focusing by an operator. Considering that the light field 6 should coincide with an X-ray field, an image position of the visible light source 1 on the light-reflecting plate 7 is coincident with the position of the X-ray source in the dental imaging apparatus radially with respect to the cylindrical inner wall surface. Of course, it is more preferred that the image position of the visible light source 1 totally coincides with the position of the X-ray source because in this way, it can be ensured that the light field 6 remains in complete coincidence with the X-ray field regardless of its distance from the area 5 to be imaged.

In some examples, an infrared sensing area is provided at a location at an edge of the light exit aperture, which does not block the visible light, or blocks it only to a minor extent, and an associated infrared sensor 9 is provided at the edge of the light exit aperture. The infrared sensor 9 includes an infrared transmitter for transmitting infrared radiation and an infrared receiver for receiving infrared radiation. By doing this, a position of a human body can be sensed to serve as a basis for controlling light emission of the visible light source 1. Specifically, when a given part of the human body, such as a hand or face, is present in a region that is irradiated with the infrared radiation from the infrared transmitter and thus allows infrared sensing, for example, 20 cm ahead, it will reflect part of the infrared radiation. After being received by the infrared receiver, this part of the infrared radiation may undergo necessary processing, and a signal may be produced, which controls the visible light source 1 to emit light, for example, for 30 seconds. Correspondingly, when the human body leaves the infrared sensing range, the visible light source 1 may stop emitting light. The infrared sensor 9 may be implemented as is conventional and, therefore, needs not be described in further detail herein.

In some examples, the light exit aperture is covered with a transparent cover 10, which has anti-glare properties and can additionally ensure accurate focusing during imaging.

To sum up, according to this embodiment, with the aid of an indication provided by visible light, a radiation field can be effectively limited, avoiding unnecessary irradiation. An operator can be helped to quickly and clearly determine an area to be irradiated with X-rays and intuitively confirm whether it is the intended area, thereby reducing the possibility of required rework and reimaging due to incorrect focusing and framing that may arise from directly performing the X-ray imaging task. This embodiment is simple and reliable in structure, requires little adaptation to conventional designs and can provide a clear indication for an X-ray field.

Embodiment 3

FIGS. 7 to 10 show a visible light projection indicator for a dental x-ray imaging apparatus, which includes a plurality of visible light sources 1 for emitting visible light in the same direction as X-rays are emitted. The visible light sources 1 are LED lights that produce soft light. An annular base 14 is also included, and the visible light sources 1 are mounted on one side of the annular base 14. On the other side of the annular base 14, there is provided a magnetic structure 12, with which it is affixed within a beam-limiting cone 3. A light passage is further included, which is provided by a double-layer cylindrical structure opening at both ends. It is essentially a space for the passage of the visible light therethrough, which is a gap between an outer surface of an inner tube 15 and an inner surface of an outer tube 16. One end of the light passage is connected to the annular base 14.

The light passage is provided at an end thereof with a transparent cover 10, which is an annular cover.

The end of the light passage is also provided with a light source switch 4. A power supply for the visible light sources 1 may be rechargeable or provided by an external power source that also powers an X-ray tube.

The outer tube 16 is nested with the inner tube 15. The outer tube 16 is disposed externally around the inner tube 15. The outer surface of the inner tube 15 and the inner surface of the outer tube 16 are reflective.

There is an X-ray source 5 for producing X-rays. The inner tube 15 and the outer tube 16 are made of materials transmissive to X-rays. In this way, they can construct the light passage that reflects visible light, while ensuring that X-rays can normally pass through it and the ultimate image quality will not be affected.

A radius of the inner tube 15 at its end proximal to the annular base 14 is smaller than its radius at its end away from the annular base 14. The inner tube 15 is shaped like a circular cone, which can better direct visible light to an exit of the beam-limiting cone 3.

Figure 10:
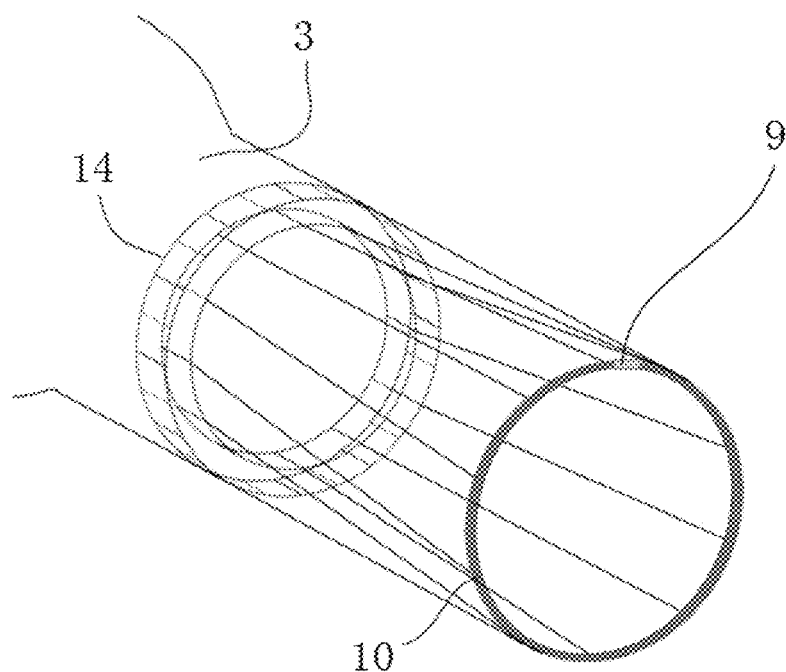
FIG. 10 is a schematic perspective assembly view of the third embodiment of the present disclosure.

The outer tube 16 is cylindrical and matches an inner wall of the beam-limiting cone 3 in terms of size and shape. As shown in FIG. 10, it can snugly fit into the beam-limiting cone 3.

The visible light sources 1 on the annular base 14 emit visible light, which travels through the light passage from one end to the other end thereof and is projected from the exit of the beam-limiting cone 3 onto a patient's face.

Figure 9:
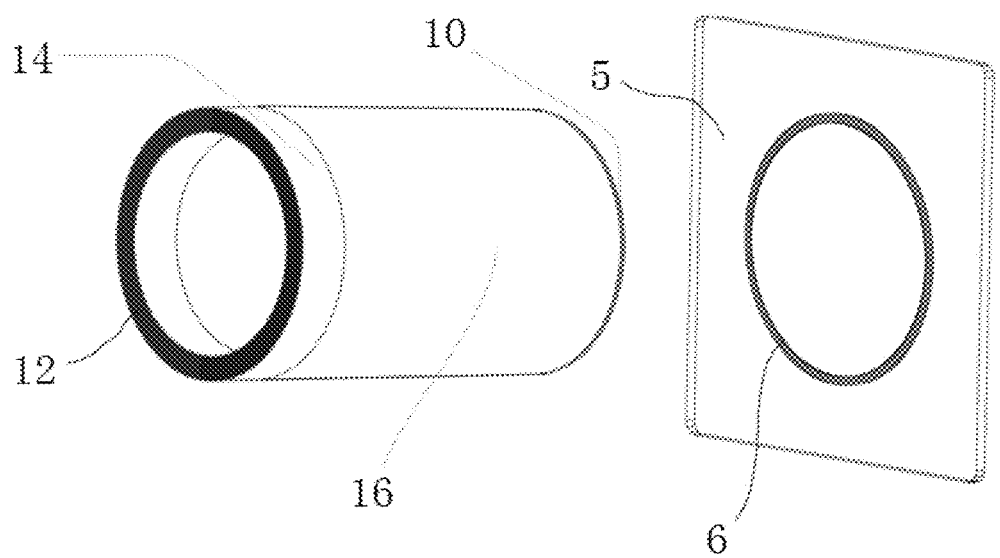
FIG. 9 schematically illustrates projection in the third embodiment of the present disclosure.

Generally, the light from the visible light sources 1 is projected on the patient's face in the form of an annular beam (light field) 6. As shown in FIG. 9, a projection target plate 5 is used to mimic the patient's face that the annular beam 6 is projected on.

Regarding a projection direction, from how the shape of a spot formed by the annular beam on the patient's face is distorted, for example, from whether it is horizontally or vertically elliptical, the projection direction can be inferred, and a possible impact of an associated projection angle on imaging can be estimated. When necessary, the projection angle may be adjusted to correct the projection direction so as to round the sport as much as possible.

The guiding visible light visualizes and reproduces the positional relationship between invisible X-rays to be projected and the site to be imaged. Thus, by using visible light, such positional relationships that have been ambiguous and have had to be speculated can now be definitively confirmed simply with the naked eye.

This embodiment provides a method of using a visible light projection indicator incorporated in a dental x-ray imaging apparatus, which includes the steps of:

a) placing the visible light projection indicator within a beam-limiting cone in the dental imaging apparatus;

b) activating a switch on the visible light projection indicator to cause the visible light projection indicator to emit visible light in the form of an annular beam;

c) according to how the shape of a spot formed by the annular visible light beam on a patient's face is distorted, for example, to whether it is horizontally or vertically elliptical, adjusting the position of the beam-limiting cone in the dental imaging apparatus and determining an area for dental imaging and a projection direction for X-rays; and d) turning on the dental imaging apparatus, carrying out X-ray exposure, removing a dental film from the patient's mouth and ending the imaging process.

According to this embodiment, the projection indicator utilizes guiding visible light to visualize, reproduce and precisely present a positional relationship between X-rays to be projected and a site to be imaged. At present, there is no alternative projection tool to this embodiment. The projection indicator of this embodiment represents a breakthrough in solving the problem of ambiguities in alignment with a target site with conventional intraoral periapical radiography, establishes a definite positional relationship for a projection direction and the size and extent of an exposure area, can accurately locate a site to be imaged and determine a projection angle and direction, and fills the theoretical void in projection technology for periapical imaging in the field of oral and maxillofacial radiography.

The projection indicator of this embodiment can be used as routine equipment in dental imaging apparatuses for X-ray projection in periapical imaging in oral and maxillofacial radiography. Firstly, the visible light projection indicator of this embodiment avoids ambiguities and operating difficulties in conventional projection techniques. Inaccurate projection will cause inconsistent image quality, and excessively long or short tooth images will bring potential hazards to clinical treatment. Secondly, imaging repetitions can be significantly reduced, effectively reducing a patient's unnecessary exposure to the harmful radiation due to such repetitions. Thirdly, the principle of accurate visible light projection is easier to understand and implement. Fourthly, it can be easily used in teaching and professional education. Fifthly, the visualization ability makes it superior to conventional projection techniques for dental imaging apparatuses and improves the theoretical system of projection technology for periapical imaging in oral and maxillofacial radiography.

In some examples, an infrared sensing area is provided at a location at an edge of the light exit aperture, which does not block the visible light, or blocks it only to a minor extent, and an associated infrared sensor 9 is provided at the edge of the light exit aperture. The infrared sensor 9 includes an infrared transmitter for transmitting infrared radiation and an infrared receiver for receiving infrared radiation. By doing this, a position of a human body can be sensed to serve as a basis for controlling light emission of the visible light sources 1. Specifically, when a given part of the human body, such as a hand or face, is present in a region that is irradiated with the infrared radiation from the infrared transmitter and thus allows infrared sensing, for example, 20 cm ahead, it will reflect part of the infrared radiation. After being received by the infrared receiver, this part of the infrared radiation may undergo necessary processing, and a signal may be produced, which controls the visible light sources 1 to emit light, for example, for 30 seconds. Correspondingly, when the human body leaves the infrared sensing range, the visible light source 1 may stop emitting light. The infrared sensor 9 may be implemented as is conventional and, therefore, needs not be described in further detail herein.

One or more technical solutions provided in this embodiment have at least the following technical effects or advantages:
1. Since visible light is used as a light source, a projection direction and the size of an exposure area can be definitely determined to enable precise location of a target site to be imaged, thereby overcoming the problem of ambiguities in target site location with conventional intraoral periapical radiography.
2. A projection direction can be accurately determined. From how the shape of a spot formed by an annular beam from the visible light projection locator on an area to be imaged is distorted, for example, from whether it is horizontally or vertically elliptical, a projection direction can be inferred, and a possible impact of an associated projection angle on imaging can be estimated. When necessary, the projection angle may be adjusted to correct the projection direction so as to round the sport as much as possible. From shape symmetry of the annular spot, the impact of the projection angle on the shape of a tooth in a captured image can be determined.
3. The principle that an area illuminated by visible light just represents a radiation field of X-rays to be projected is easier to understand and implement for medical practitioners and can facilitate teaching and education.

Embodiment 4

Figure 11:
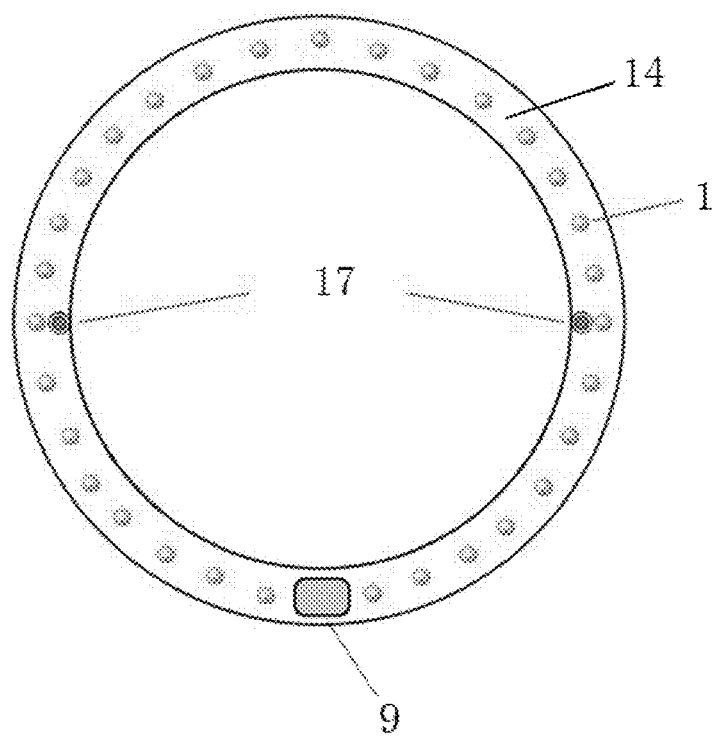
FIG. 11 is a schematic perspective view of an example of a fourth embodiment of the present disclosure.

FIG. 11 shows a visible light projection indicator for a dental x-ray imaging apparatus, which includes a base 14. The base 14 is an annular structure defining a central hollow. A plurality of visible light sources 1 for emitting visible light is provided on one side of the base 14. The visible light sources 1 are LED lights that are soft light sources.

Two intersection lights 17 are also included. The two intersection lights 17 are disposed at symmetrical locations on the base, which are spaced apart 180°. The intersection lights 17 are laser lights, which produce beams intersecting 5-10 cm ahead.

With the aid of the base, the visible light projection indicator is fitted over an outer circumference of a beam-limiting cone 3 in the dental imaging apparatus, generally at a trailing end of the beam-limiting cone 3. The trailing end refers to an end farther away from an X-ray source.

In general terms, the X-ray source is deployed at a distance of at least greater than 20 cm away from a patient's skin. Considering a length of the beam-limiting cone 3 and that its distance from the skin is required to take prevention and control of nosocomial infection and other factors into account, the intersection for the intersection lights is most preferred to be located about 5-10 cm ahead of the beam-limiting cone 3. Such locations are suitable for a target site of the facial skin, where the center of a circular radiation field to be formed is desired to be located. Only the range of 5-10 cm allows intersection of the projected beams at a single point, and any other location ahead of or behind said center will lead to two intersections in the radiation field.

Figure 12:
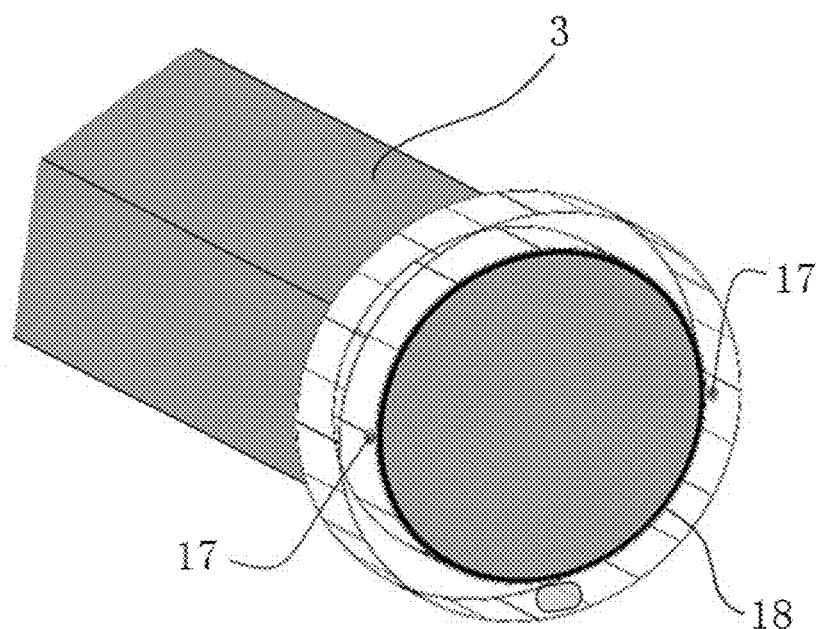
FIG. 12 is a schematic assembly view of an example of the fourth embodiment of the present disclosure.

In some examples, as shown in FIG. 12, the base 14 is an integral structure provided on an inner surface thereof with a first elastic member 18, with which the base 14 can be fitted over the outer circumference of the beam-limiting cone 3 so that it is affixed to the beam-limiting cone 3. The first elastic member 18 is usually made of rubber.

Dimensions of the central hollow of the integral annular base 14 may be determined according to dimensions of the beam-limiting cone 3 in the dental imaging apparatus. Alternatively, dimensions of the first elastic member 18 may be adjusted to enable matching of the two. In this way, projection indicators of various sizes can be used.

Light is emitted from the visible light sources 1 in the form of an annular light beam, which travels in a direction in which X-rays are to be projected and forms an annular spot on a surface of an object.

Figure 13:
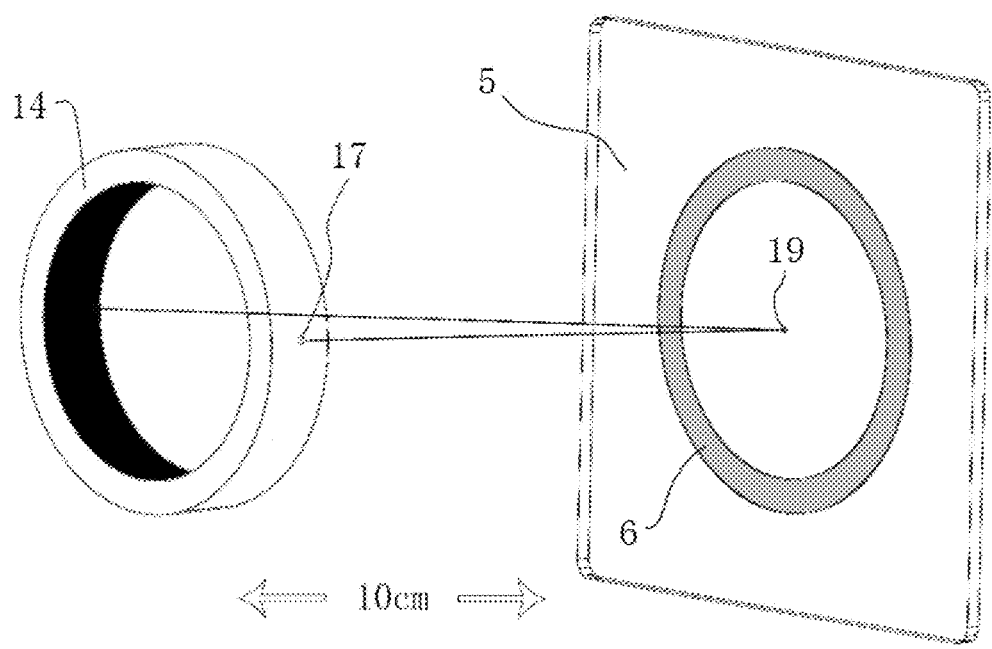
FIG. 13 schematically illustrates spots formed on a projection target plate by light from an annular light and intersection lights in an indicator of FIG. 11.
Figure 14:
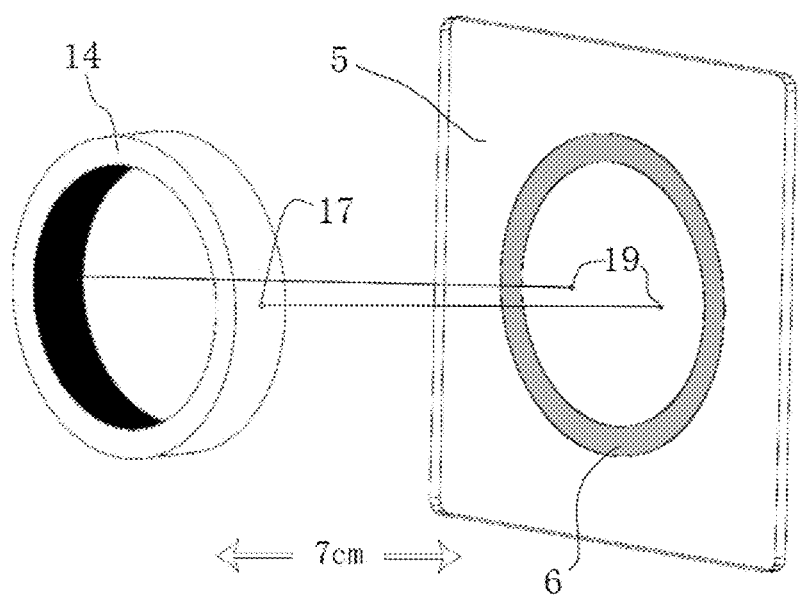
FIG. 14 schematically illustrates spots formed on a projection target plate by light from the annular light and the intersection lights in the indicator of FIG. 11.

Light from the integral annular light is projected onto a projection target plate 5 and forms thereon an integral annular spot 6. Light beams 19 emitted from the two intersection lights 17 intersect at a center of a circular radiation field. This occurs only 5-10 cm ahead (see FIG. 13), and any other location ahead of or behind said center will lead to two intersections in the radiation field (see FIG. 14).

The integral annular base may be also provided with a cover in front of the light sources.

Figure 15:
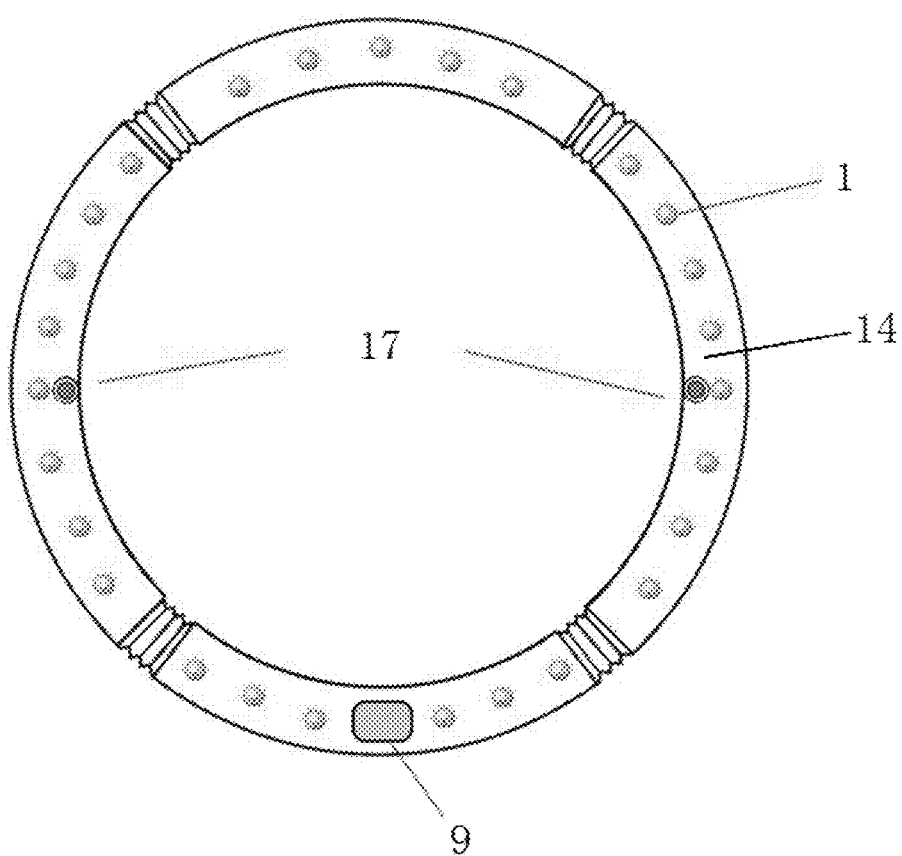
FIG. 15 is a schematic perspective view of another example of the fourth embodiment of the present disclosure.

In some examples, the annular base 14 is a split structure, as shown in FIG. 15.

Figure 16:
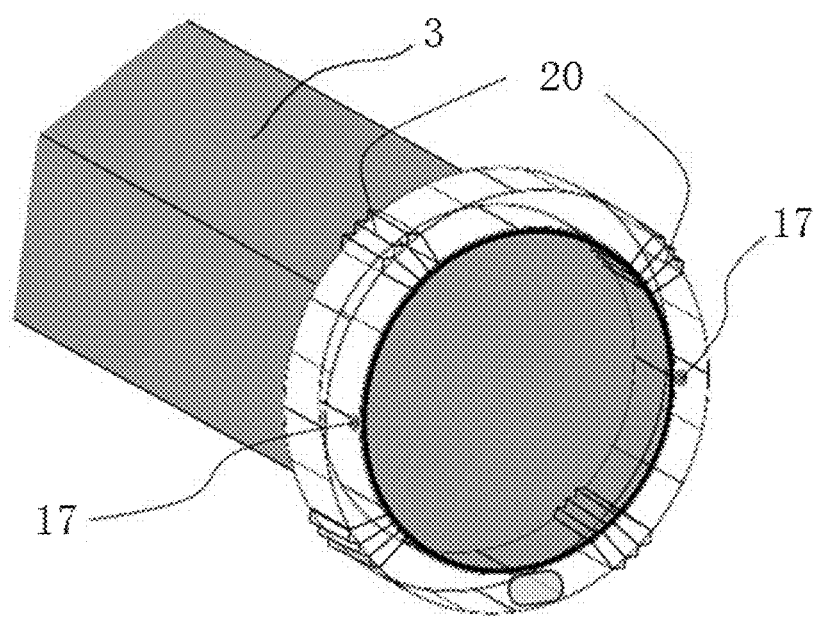
FIG. 16 is a schematic assembly view of the other example of the fourth embodiment of the present disclosure.

The split annular base 14 consists of a number of segments. As shown in FIG. 16, adjacent segments are connected together with second elastic members 20 to form the base 14, which is then fitted over the outer circumference of the beam-limiting cone 3 so that it is affixed to the beam-limiting cone 3.

The second elastic members 20 are connecting members made of an elastic material or stretchable and contractible ring sections.

Connecting the arc-shaped light source segments with an elastic material or with stretchable and contractible ring sections enables the base to be used with beam-limiting cones 3 of various specifications.

The elasticity of the second elastic members 20 imparts elasticity to the split annular base 14, enabling its use with beam-limiting cones 3 of various specifications. In each case, the base 14 can be affixed to the beam-limiting cone 3.

Figure 17:
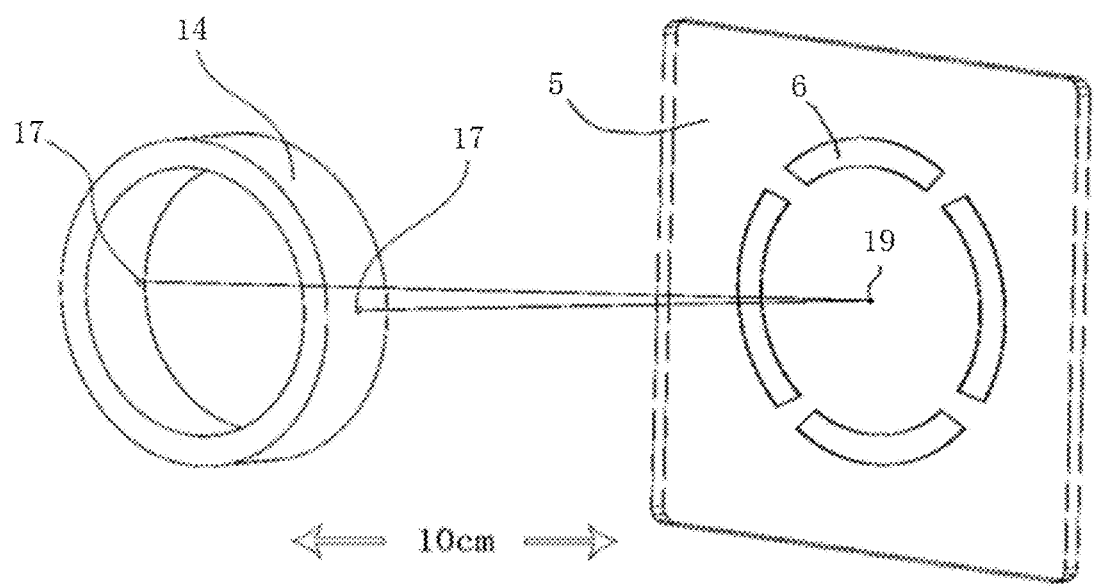
FIG. 17 schematically illustrates spots formed on a projection target plate by light from an annular light and intersection lights in an indicator of FIG. 15.
Figure 18:
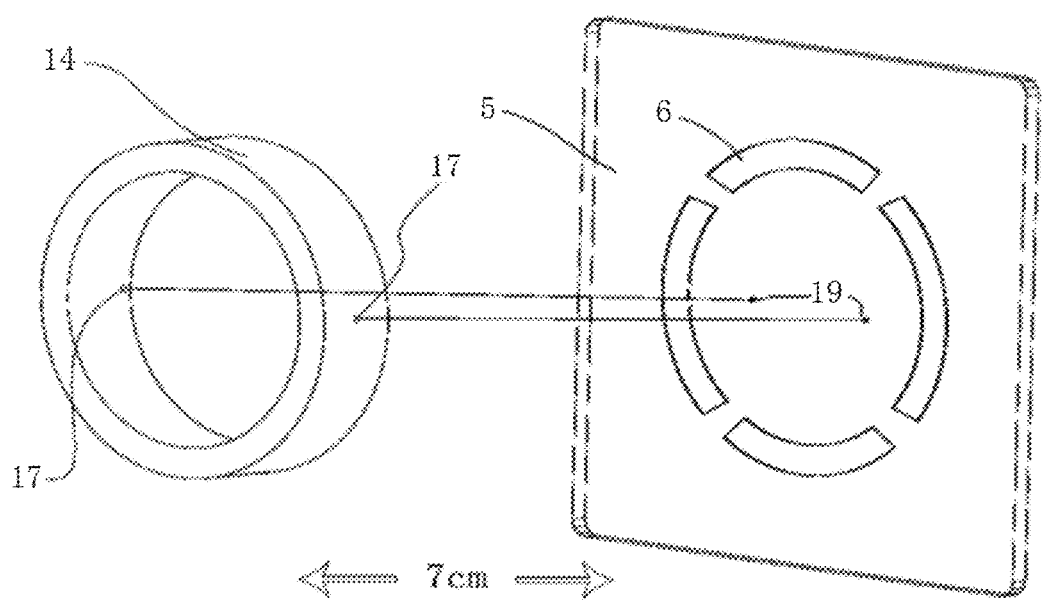
FIG. 18 schematically illustrates spots formed on a projection target plate by light from the annular light and the intersection lights in the indicator of FIG. 15.

As shown in FIGS. 17 and 18, light from the split annular light is projected onto a projection target plate 5 and forms thereon spots in the form of separate segments of an annulus.

Light beams 19 emitted from the two intersection lights 17 intersect at a center of a circular radiation field. This occurs only 5-10 cm ahead (see FIG. 17), and any other location ahead of or behind said center will lead to two intersections in the radiation field (see FIG. 18).

The visible light sources 1 are soft light sources. The split annular base 14 is provided with an arc-shaped covers in front of the light sources 1.

A power supply for the visible light sources 1 and the two intersection lights 17 are USB rechargeable via a USB port. The visible light sources 1 are implemented as 15-25 W LED lights, and the two intersection lights 17 as 5-20 mW red laser diodes.

A method of using the visible light projection indicator for a dental x-ray imaging apparatus according to this embodiment includes the steps of:
- a) at first, mounting the barrel-like visible light projection indicator at a trailing end of a beam-limiting cone;
- b) a light source switch on the visible light projection indicator to cause visible light to be projected from the visible light projection indicator onto a patient's face;
- c) adjusting the symmetrical intersection lights that are spaced apart 180° and determining a distance between the beam-limiting cone in the dental imaging apparatus and the patient's face;
- d) according to the shape of an annular spot formed by the visible light and to a distortion in the shape, adjusting the position of the beam-limiting cone in the dental imaging apparatus and determining an area for dental imaging; and
- e) turning on the dental imaging apparatus, carrying out X-ray exposure, removing a dental film from the patient's mouth and ending the imaging process.

As shown in FIGS. 11, 12, 15 and 16, an infrared sensing area is provided at a location at an edge of the light exit aperture, which does not block the visible light, or blocks it only to a minor extent, and an associated infrared sensor 9 is provided at the edge of the light exit aperture. The infrared sensor 9 includes an infrared transmitter for transmitting infrared radiation and an infrared receiver for receiving infrared radiation. By doing this, a position of a human body can be sensed to serve as a basis for controlling light emission of the visible light sources 1. Specifically, when a given part of the human body, such as a hand or face, is present in a region that is irradiated with the infrared radiation from the infrared transmitter and thus allows infrared sensing, for example, 20 cm ahead, it will reflect part of the infrared radiation. After being received by the infrared receiver, this part of the infrared radiation may undergo necessary processing, and a signal may be produced, which controls the visible light sources 1 to emit light, for example, for 30 seconds. Correspondingly, when the human body leaves the infrared sensing range, the visible light source 1 may stop emitting light. The infrared sensor 9 may be implemented as is conventional and, therefore, needs not be described in further detail herein.

One or more technical solutions provided in this embodiment have at least the following technical effects or advantages:
1. Since two types of visible light are used in combination as a light source, a projection direction and the size of an exposure area can be definitely determined to enable precise location of a target site to be imaged, thereby overcoming the problem of ambiguities in target site location with conventional intraoral periapical radiography.
2. A projection direction can be accurately determined. From how the shape of a spot formed by an annular beam from the visible light projection locator on an area to be imaged is distorted, for example, from whether it is horizontally or vertically elliptical, a projection direction can be inferred, and a possible impact of an associated projection angle on imaging can be estimated. When necessary, the projection angle may be adjusted to correct the projection direction so as to round the sport as much as possible. From shape symmetry of the annular spot, the impact of the projection angle on the shape of a tooth in a captured image can be determined.
3. The principle that an area illuminated by the combined two types of visible light represents a radiation field of X-rays to be projected is easier to understand and implement for medical practitioners and can facilitate teaching and education.

Preferred specific embodiments have been described in detail above. It is to be understood that, those of ordinary skill in the art, without the need for creative effort, can make various modifications and changes, based on the concept of the present invention. Accordingly, all the technical solutions that can be obtained by those skilled in the art by logical analysis, inference or limited experimentation in accordance with the concept of the invention on the basis of the prior art are intended to fall within the protection scope as defined by the claims.

The invention claimed is:

1. A visible light projection indicator for a dental x-ray imaging apparatus, comprising:
   a casing, one end of the casing detachably affixed to a beam-limiting cone in the dental x-ray imaging apparatus, the other end thereof provided with a light exit aperture;
   a visible light source positioned in the casing and configured to be able to emit visible light;
   a light passage being formed after the casing is affixed to the beam-limiting cone so that visible light emitted from the visible light source is able to travel along the light passage and exits from the light exit aperture;
   wherein the casing comprises an annular base, and the visible light source is mounted in the annular base;
   wherein the casing further comprises a double-layer cylindrical structure connected to openings at opposing ends of the annular base, the double-layer cylindrical structure comprising an inner tube disposed on an inner side and an outer tube disposed on an outer side, the light passage being formed between an outer surface of the inner tube and an inner surface of the outer tube.

2. The visible light projection indicator according to claim 1, wherein the light exit aperture is covered with a transparent cover.

3. The visible light projection indicator according to claim 2, wherein the transparent cover is provided at its center with a light-shading mark for indicating an area where the visible light is projected.

4. The visible light projection indicator according to claim 1, wherein a magnetic structure is provided on an end face of the casing opposing the light exit aperture, and the casing is configured to be able to be attractively affixed to the beam-limiting cone through the magnetic structure.

5. The visible light projection indicator according to claim 1, wherein the visible light source is arranged on an inner wall of the casing, and the casing is provided therein with a light-reflecting plate, which is placed obliquely with respect to the inner wall of the casing so that a position of a virtual image of the visible light source formed by the light-reflecting plate coincides with a position of an X-ray source in the dental x-ray imaging apparatus in a direction perpendicular to an opening of the beam-limiting cone.

6. The visible light projection indicator according to claim 5, further comprising a convex lens disposed between the light-reflecting plate and the light exit aperture.

7. The visible light projection indicator according to claim 1, wherein the outer surface of the inner tube and the inner surface of the outer tube are made of a reflective material.

8. The visible light projection indicator according to claim 1, wherein the inner tube has a smaller radius at one end proximal to the annular base than at one end away from the annular base.

9. The visible light projection indicator according to claim 1, further comprising two laser light sources being respectively arranged on the annular base and radially symmetrical with respect to a center of the annular base, an intersection of light beams emitted by the two laser light sources being located ahead of the light exit aperture.

10. The visible light projection indicator according to claim 1, wherein the annular base is provided on an inner surface thereof with a first elastic member.

11. The visible light projection indicator according to claim 1, wherein the annular base comprises a plurality of base elements, each of the base elements being connected to each other by second elastic members.

12. A dental x-ray imaging apparatus, comprising:
an X-ray source;
a body for housing the X-ray source;
a beam-limiting cone disposed externally around the X-ray source and extending out of the body;
a visible light projection indicator comprising: a casing, one end of the casing affixed to the beam-limiting cone, the other end thereof provided with a light exit aperture; a visible light source positioned in the casing and configured to be able to emit visible light; a light passage being formed after the casing is affixed to the beam-limiting cone so that visible light emitted from the visible light source is able to travel along the light passage and exits from the light exit aperture;
wherein the casing comprises an annular base, and the visible light source is mounted in the annular base;
wherein the casing further comprises a double-layer cylindrical structure connected to openings at opposing ends of the annular base, the double-layer cylindrical structure comprising an inner tube disposed on an inner side and an outer tube disposed on an outer side, the light passage being formed between an outer surface of the inner tube and an inner surface of the outer tube.

13. The dental x-ray imaging apparatus according to claim 12, wherein the visible light source is arranged on an inner wall of the casing, and the casing is provided therein with a light-reflecting plate, which is placed obliquely with respect to the inner wall of the casing so that a position of a virtual image of the visible light source formed by the light-reflecting plate coincides with a position of the X-ray source in a direction perpendicular to an opening of the beam-limiting cone.

14. The dental x-ray imaging apparatus according to claim 13, further comprising a convex lens disposed between the light-reflecting plate and the light exit aperture.

15. The dental x-ray imaging apparatus according to claim 12, further comprising two laser light sources being respectively arranged on the annular base and radially symmetrical with respect to a center of the annular base, an intersection of light beams emitted by the two laser light sources being located ahead of the light exit aperture.

* * * * *